(12) United States Patent
Harper et al.

(10) Patent No.: US 9,469,851 B2
(45) Date of Patent: Oct. 18, 2016

(54) RECOMBINANT VIRUS PRODUCTS AND METHODS FOR INHIBITION OF EXPRESSION OF DUX4

(75) Inventors: Scott Quenton Harper, Powell, OH (US); Jian Liu, Los Angeles, CA (US); Sara Garwick Coppens, Hilliard, OH (US); Lindsay Wallace, Columbus, OH (US)

(73) Assignee: NATIONWIDE CHILDREN'S HOSPITAL, INC., Columbus, OH (US)

( * ) Notice: Subject to any disclaimer, the term of this patent is extended or adjusted under 35 U.S.C. 154(b) by 94 days.

(21) Appl. No.: 14/234,413

(22) PCT Filed: Jul. 24, 2012

(86) PCT No.: PCT/US2012/047999
§ 371 (c)(1),
(2), (4) Date: Jul. 14, 2014

(87) PCT Pub. No.: WO2013/016352
PCT Pub. Date: Jan. 31, 2013

(65) Prior Publication Data
US 2014/0322169 A1    Oct. 30, 2014

Related U.S. Application Data

(60) Provisional application No. 61/511,319, filed on Jul. 25, 2011.

(51) Int. Cl.
| | |
|---|---|
| *C12N 15/86* | (2006.01) |
| *C12N 15/09* | (2006.01) |
| *C12N 15/63* | (2006.01) |
| *C12N 15/11* | (2006.01) |
| *C12N 15/113* | (2010.01) |

(52) U.S. Cl.
CPC ............. *C12N 15/113* (2013.01); *C12N 15/86* (2013.01); *C12N 2310/11* (2013.01); *C12N 2310/141* (2013.01); *C12N 2320/30* (2013.01); *C12N 2330/51* (2013.01); *C12N 2750/00032* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 5,173,414 A | 12/1992 | Lebkowski et al. |
| 5,658,776 A | 8/1997 | Flotte et al. |
| 5,786,211 A | 7/1998 | Johnson |
| 5,871,982 A | 2/1999 | Wilson et al. |
| 6,258,595 B1 | 7/2001 | Gao et al. |
| 6,566,118 B1 | 5/2003 | Atkinson et al. |
| 2005/0260603 A1 | 11/2005 | DeNise et al. |
| 2006/0246491 A1 | 11/2006 | Srivastava |
| 2011/0130442 A1* | 6/2011 | Kosaka et al. ............. 514/44 A |

FOREIGN PATENT DOCUMENTS

| | | |
|---|---|---|
| WO | WO-95/13392 A1 | 5/1995 |
| WO | WO-96/17947 A1 | 6/1996 |
| WO | WO-97/08298 A1 | 3/1997 |
| WO | WO-97/09441 A2 | 3/1997 |
| WO | WO-97/21825 A1 | 6/1997 |
| WO | WO-98/09657 A2 | 3/1998 |
| WO | WO-99/11764 A2 | 3/1999 |
| WO | WO-2008/067480 | 6/2008 |

OTHER PUBLICATIONS

Shanks et al, Are animal models predictive for humans? Philosophy, Ethics, and Humanities in Medicine, 2009, pp. 1-20.*
Daya et al, Gene Therapy using Adeno-Associated Virus Vectors, Clin Microbiol Rev, 2008, pp. 583-593.*
Opalinska and Gewirtz, Nucleic-Acid Therapeutics: Basic Principles and Recent Applications, Nature Reviews, 2002, vol. 1, pp. 503-514.*
Zhang et al, Human skeletalmuscle xenograft as a new preclinical model for muscle disorders, Human Molecular Genetics, 2014, vol. 23, No. 12 3180-3188.*
Carter, Adeno-associated virus vectors, Curr. Opin. Biotechnol., 3(5):533-9 (1992).
Clark et al., A stable cell line carrying adenovirus-inducible rep and cap genes allows for infectivity titration of adeno-associated virus vectors, Gene Ther., 3(12):1124-32 (1996).
Cserjesi et al., Myogenin induces the myocyte-specific enhancer binding factor MEF-2 independently of other muscle-specific gene products, Mol. Cell Biol., 11(10):4854-62 (1991).
De et al.,High Levels of Persistent Expression of 1-Antitrypsin Mediated by the Nonhuman Primate Serotype rh. 10 Adeno-associated Virus Despite Preexisting Immunity to Common Human Adeno-associated Viruses, Mol. Ther., 13(1):67-76 (2006).
Duan (ed.), Muscle Gene Therapy, Section 7.3 of Chapter 7, Springer Science + Business Media LLC (2010).
Fechner et al., Cardiac-targeted RNA interference mediated by an AAV9 vector improves cardiac function in coxsackievirus B3 cardiomyopathy, J. Mol. Med. (Berl.), 86(9):987-97 (2008).
Gao et al., Clades of Adeno-associated viruses are widely disseminated in human tissues, J. Virol., 78(12):6381-8 (2004).
GenBank CR044042, Reverse strand read from insert in 3'HPRT insertion targeting and chromosome engineering clone MHPP102d13, genomic survey sequence, Jul. 9, 2004 [online]. Retrieved on Sep. 25, 2012, from the Internet at:URL:http://www.ncbi.nlm.nih.gov/nucgss/CR044042>.

(Continued)

Primary Examiner — Maria Marvich
(74) Attorney, Agent, or Firm — Marshall, Gerstein & Borun LLP

(57) ABSTRACT

The present invention relates to RNA interference-based methods for inhibiting the expression of the DUX4 gene, a double homeobox gene on human chromosome 4q35. Recombinant adeno-associated viruses of the invention deliver DNAs encoding microRNAs that knock down the expression of DUX4. The methods have application in the treatment of muscular dystrophies such as facioscapulohumeral muscular dystrophy.

5 Claims, 5 Drawing Sheets

(56) References Cited

OTHER PUBLICATIONS

GenBank DU276454, 1098448058383 CHORI-243 Ovis arles genomic clone CH243-186D9, genomic survey sequence, May 15, 2010 [online]. Retrieved on Sep. 25, 2012, from the internet: <URL:http://www.ncbi.nlm.nih.gov/nucgss/DU276454>.
Hermonat et al., Use of adeno-associated virus as a mammalian DNA cloning vector: transduction of neomycin resistance into mammalian tissue culture cells, Proc. Natl. Acad. Sci. USA, 81(20):6466-70 (1984).
Johnson et al., Muscle creatine kinase sequence elements regulating skeletal and cardiac muscle expression in transgenic mice, Mol. Cell Biol., 9(8):3393-9 (1989).
Laughlin et al., Cloning of infectious adeno-associated virus genomes in bacterial plasmids, Gene, 23(1):65-73 (1983).
Lebkowski et al., Adeno-associated virus: a vector system for efficient introduction and integration of DMA into a variety of mammalian cell types, Mol. Cell Biol., 9(10:3988 (1988).
Lemmers et al., A Unifying Genetic Model for Facioscapulohumeral Muscular Dystrophy, Science, 329 (5999:1650-3 (Sep. 24, 2010).
Mader et al., A steroid-inducible promoter for the controlled overexpression of cloned genes in eukaryotic cells, Proc. Natl. Acad. Sci. USA, 90(12):5603-7 (1993).
McLaughlin et al., Adeno-associated virus general transduction vectors: analysis of proviral structures, J. Virol., 62(6):1963-73 (1988).
Mori et al., Two novel adeno-associated viruses from cynomolgus monkey: pseudotyping characterization of capsid protein, Virology, 330(2):375-83 (2004).
Muscat et al., Multiple 5'-flanking regions of the human alpha-skeletal actin gene synergistically modulate muscle-specific expression, Mol. Cell Biol., 7(11):4089-99 (1987).
Muzyczka, Use of adeno-associated virus as a general transduction vector for mammalian cells, Curr. Top. Microbiol. Immunol., 158:97-129 (1992).
Neguembor et al., In junk we trust: repetitive DNA, epigenetics and facioscapulohumeral muscular dystrophy, Epigenomics, 2(2):271-87 (2010).
Perrin et al., An experimental rabies vaccine produced with a new BHK-21 suspension cell culture process: use of serum-free medium and perfusion-reactor system, Vaccine, 13(13):1244-50 (1995).
Samulski et al., Helper-free stocks of recombinant adeno-associated viruses: normal integration does not require viral gene expression, J. Virol., 63(9):3822-8 (1989).
Schnepp et al., Highly purified recombinant adeno-associated virus vectors. Preparation and quantitation, Methods Mol. Med., 69:427-43 (2002).
Semenza et al., Hypoxia-inducible nuclear factors bind to an enhancer element located 3' to the human erythropoietin gene, Proc. Natl. Acad. Sci. USA, 88(13):5680-4 (1991).
Senapathy et al., Molecular cloning of adeno-associated virus variant genomes and generation of infectious virus by recombination in mammalian cells, J. Biol. Chem., 259(7):4661-6 (1984).
Tratschin et al., A human parvovirus, adeno-associated virus, as a eucaryotic vector: transient expression and encapsidation of the procaryotic gene for chloramphenicol acetyltransferase, Mol. Cell Biol., 4:2072-81 (1984).
Tratschin et al., Adeno-associated virus vector for high-frequency integration, expression, and rescue of genes in mammalian cells, Mol. Cell Biol., 5(11):3251-60 (1985).
Wallace et al., Developing RNAi Therapy for FSHD, Mol. Ther., 17(Suppl 1):S151 (2009).
Wei et al., Therapeutic RNAi for dominant muscle disease, Mol. Ther., 17(Suppl 1):S200 (2009).
Weintraub et al., The myoD gene family: nodal point during specification of the muscle cell lineage, Science, 251(4995):761-6 (1991).
Wuebbles et al., Testing the effects of FSHD candidate gene expression in vertebrate muscle development, Int. J. Clin. Exp. Pathol., 3(4):386-400 (2010).
Xiao et al., Production of high-titer recombinant adeno-associated virus vectors in the absence of helper adenovirus, J. Virol., 72(3):2224-32 (1998).
Kowaljow et al., The DUX4 gene at the FSHD1A locus encodes a pro-apoptotic protein, Neuromuscular Disorders, 17(8):611-23 (2007).
Supplementary European Search Report, European Patent Application No. EP12816988, dated Mar. 10, 2015.
Vanderplanck et al., Keynote 5: Suppression of DUX4 or DUX4C expression by antisense strategies in a therapeutic approach for FSHD, J. Gene Med., 13(7-8):414 (2011).
Vanderplanck et al., The FSHD atrophic myotube phenotype is caused by DUX4 expression, PLOS One, 6(10):e26820 (2011).
Wallace et al., RNA interference inhibits DUX4-induced muscle toxicity in vivo: implications for a targeted FSHD therapy, Mol. Ther., 20(7):1417-23 (2012).
Wei et al., Therapeutic RNAi for dominant muscle disease, Mol. Ther., 17(Suppl 1):S200-S201 (2009).

* cited by examiner

Figure 1

```
ccaccccccc ccccaccac caccaccacc accacccgc cggccggccc caggcctcga 61
cgccctgggt cccttccggg gtggggcggg ctgtcccagg ggggctcacc gccattcatg 121
aaggggtgga gcctgcctgc ctgtgggcct ttacaagggc ggctggctgg ctggctggct 181
gtccgggcag gcctcctggc tgcacctgcc gcagtgcaca gtccggctga ggtgcacggg 241
agcccgccgg cctctctctg cccgcgtccg tccgtgaaat tccggccggg gctcaccgcg 301
atggccctcc cgacaccctc ggacagcacc ctcccgcgg aagcccgggg acgaggacgg 361
cgacggagac tcgtttggac cccgagccaa agcgaggccc tgcgagcctg ctttgagcgg 421
aacccgtacc cgggcatcgc caccagagaa cggctggccc aggccatcgg cattccggag 481
cccagggtcc agatttggtt tcagaatgag aggtcacgcc agctgaggca gcaccggcgg 541
gaatctcggc cctggcccgg gagacgcggc ccgccagaag gccggcgaaa gcggaccgcc 601
gtcaccggat cccagaccgc cctgctcctc cgagcctttg agaaggatcg ctttccaggc 661
atcgccgccc gggaggagct ggccagagag acgggcctcc cggagtccag gattcagatc 721
tggtttcaga atcgaagggc caggcacccg ggacaggtg gcagggcgcc cgcgcaggca 781
ggcggcctgt gcagcgcggc ccccggcggg ggtcaccctg ctccctcgtg ggtcgccttc 841
gcccacaccg gcgcgtgggg aacggggctt cccgcacccc acgtgccctg cgcgcctggg 901
gctctcccac aggggctt cgtgagccag gcagcgaggg ccgcccccgc gctgcagccc 961
agccaggccg cgccggcaga gggggtctcc caacctgccc cggcgcgcgg ggatttcgcc 1021
tacgccgccc cggctcctcc ggacgggcg ctctcccacc ctcaggctcc tcggtggcct 1081
ccgcacccgg gcaaaagccg ggaggaccgg gacccgcagc gcgacggcct gccgggcccc 1141
tgcgcggtgg cacagcctgg gcccgctcaa gcggggccgc agggccaagg ggtgcttgcg 1201
ccacccacgt cccaggggag tccgtggtgg ggctggggcc ggggtcccca ggtcgccggg 1261
gcggcgtggg aacccaagc cggggcagct ccacctcccc agcccgcgcc cccggacgcc 1321
tccgcctccg cgcggcaggg gcagatgcaa ggcatcccgg cgccctccca ggcgctccag 1381
gagccggcgc cctggtctgc actcccctgc ggcctgctgc tggatgagct cctggcgagc 1441
ccggagtttc tgcagcaggc gcaacctctc ctagaaacgg aggccccggg ggagctggag 1501
gcctcggaag aggccgcctc gctggaagca cccctcagcg aggaagaata ccgggctctg 1561
ctggaggagc tttaggacgc ggggttggga cggggtcggg tggttcgggg cagggcg
```

SEQ ID NO: 7

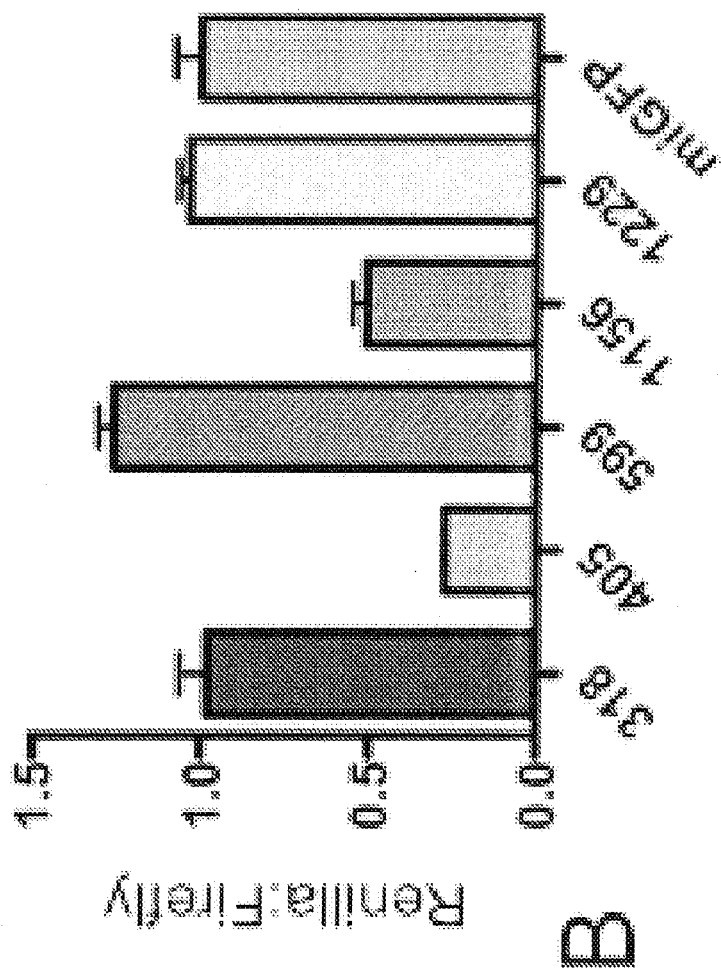
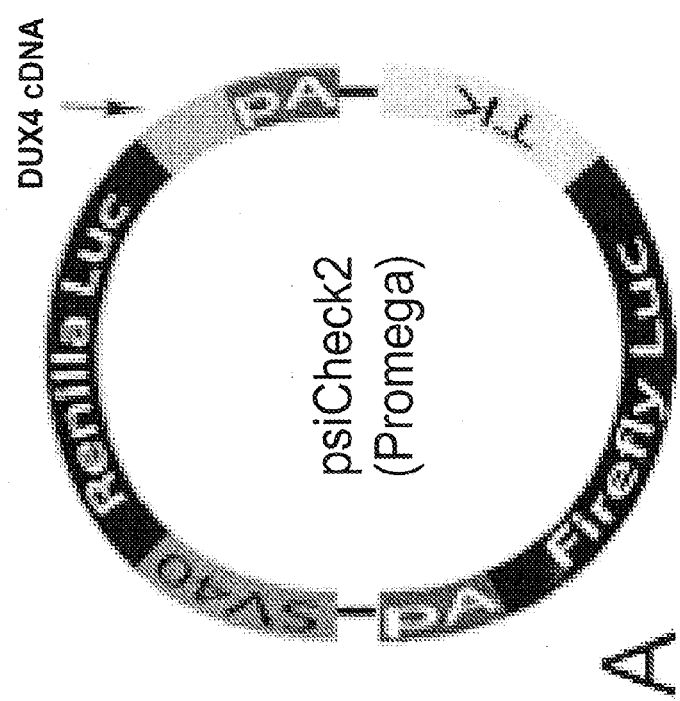
Figure 3A
Figure 3B

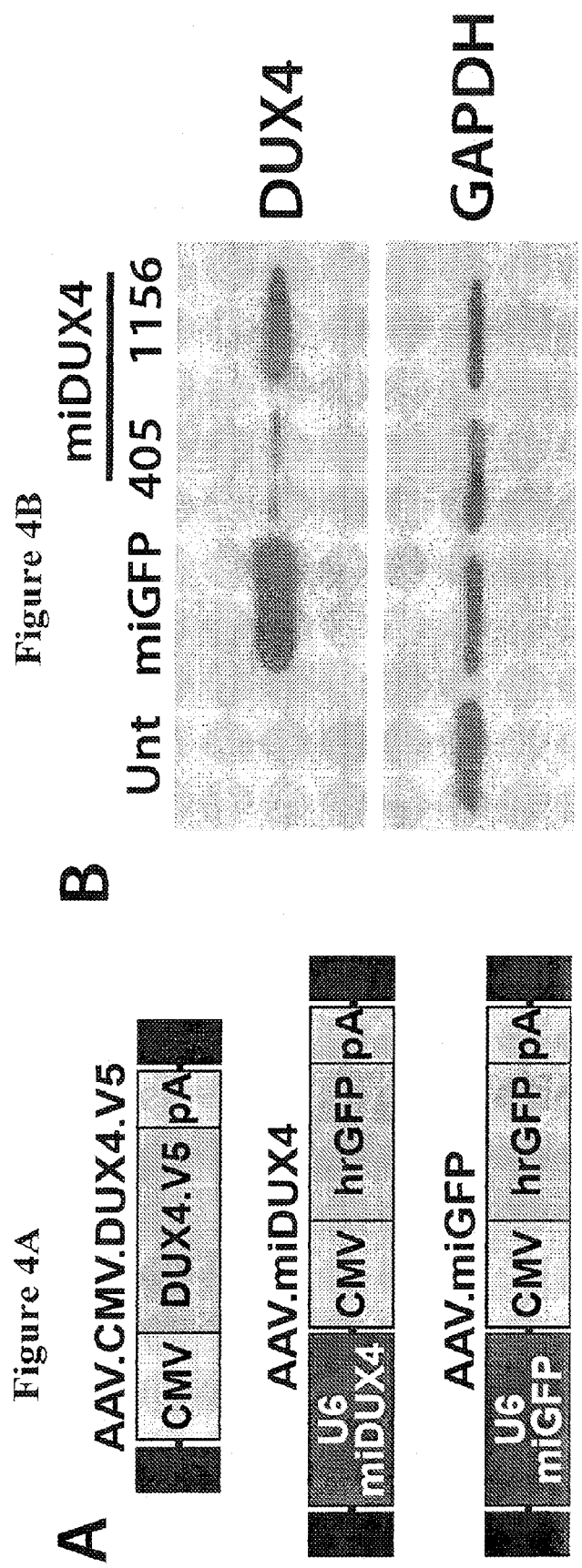

RECOMBINANT VIRUS PRODUCTS AND METHODS FOR INHIBITION OF EXPRESSION OF DUX4

This application claims the benefit of the filing date of U.S. Provisional Patent Application No. 61/511,319 filed Jul. 25, 2011, which is incorporated by reference herein in its entirety.

FIELD OF THE INVENTION

The present invention relates to RNA interference-based methods for inhibiting the expression of the DUX4 gene, a double homeobox gene on human chromosome 4q35. Recombinant adeno-associated viruses of the invention deliver DNAs encoding microRNAs that knock down the expression of DUX4. The methods have application in the treatment of muscular dystrophies such as facioscapulohumeral muscular dystrophy.

INCORPORATION BY REFERENCE OF THE SEQUENCE LISTING

This application contains, as a separate part of disclosure, a Sequence Listing in computer-readable form (filename: 45714PCT_SeqListing.txt; 1,661,020 bytes—ASCII text file) which is incorporated by reference herein in its entirety.

BACKGROUND

Muscular dystrophies (MDs) are a group of genetic diseases. The group is characterized by progressive weakness and degeneration of the skeletal muscles that control movement. Some forms of MD develop in infancy or childhood, while others may not appear until middle age or later. The disorders differ in terms of the distribution and extent of muscle weakness (some forms of MD also affect cardiac muscle), the age of onset, the rate of progression, and the pattern of inheritance.

Facioscapulohumeral muscular dystrophy (FSHD) is a complex autosomal dominant disorder characterized by progressive and asymmetric weakness of facial, shoulder and limb muscles. Symptoms typically arise in adulthood with most patients showing clinical features before age thirty. About five percent of patients develop symptoms as infants or juveniles and these are generally more severely affected. Clinical presentation can vary from mild (some limited muscle weakness) to severe (wheelchair dependence). Historically, FSHD was classified as the third most common MD, affecting one in 20,000 individuals worldwide. However, recent data indicate FSHD is the most common MD in Europe, suggesting its worldwide incidence may be underestimated.

Typical FSHD cases (FSHD1A, heretofore referred to as FSHD) are linked to heterozygous chromosomal deletions that decrease the copy number of 3.3 kilobase (kb) D4Z4 repeats on human chromosome 4q35. Simplistically, normal individuals have 11-100 tandemly-repeated D4Z4 copies on both 4q35 alleles, while patients with FSHD have one normal and one contracted allele containing 1-10 repeats. In addition FSHD-associated D4Z4 contractions must occur on specific disease-permissive chromosome 4q35 backgrounds. Importantly, no genes are completely lost or structurally mutated as a result of FSHD-associated deletions. Thus, although the disease was formally classified in 1954, and the primary genetic defect identified in 1992, the pathogenic mechanisms remain unresolved.

In leading FSHD pathogenesis models, D4Z4 contractions are proposed to cause epigenic changes that permit expression of genes with myopathic potential. As a result, aberrant over-expression of otherwise silent or near-silent genes may ultimately cause MD. This model is consistent with data showing normal 4q35 D4Z4 repeats have heterochromatin characteristics, while FSHD-linked D4Z4 repeats contain marks more indicative of actively transcribed euchromatin. These transcription-permissive epigenetic changes, coupled with the observation that complete monosomic D4Z4 deletions (i.e., zero repeats) do not cause FSHD, support the hypothesis that D4Z4 repeats harbor potentially myopathic open reading frames (ORFs), which are abnormally expressed in FSHD muscles. This notion was initially considered in 1994, when a D4Z4-localized ORF, called DUX4, was first identified. However, the locus had some characteristics of an unexpressed pseudogene and DUX4 was therefore summarily dismissed as an FSHD candidate. For many years thereafter, the search for FSHD-related genes was mainly focused outside the D4Z4 repeats, and although some intriguing candidates emerged from these studies, no single gene has been conclusively linked to FSHD development. This slow progress led to the re-emergence of DUX4 as an FSHD candidate in 2007. Even as of 2010 though, researchers continued to highlight other genes as candidates. See, for example, Wuebbles et al., *Int. J. Clin. Exp. Pathol.*, 3(4): 386-400 (2010) highlighting the FSHD region gene 1 (frg1). In contrast, Wallace et al., *Mol. Ther.*, 17(Suppl. 1): S151 (2009); Wei et al., *Mol. Ther.*, 17(Suppl. 1): S200 (2009); and the Lemmers et al. report from the *Sciencexpress* issue of Aug. 19, 2010 highlight DUX4. Neguembor and Gabellini, *Epigenomics*, 2(2): 271-287 (2010) is a recent review article regarding FSHD.

RNA interference (RNAi) is a mechanism of gene regulation in eukaryotic cells that has been considered for the treatment of various diseases. RNAi refers to post-transcriptional control of gene expression mediated by microRNAs (miRNAs). The miRNAs are small (21-25 nucleotides), noncoding RNAs that share sequence homology and base-pair with 3' untranslated regions of cognate messenger RNAs (mRNAs). The interaction between the miRNAs and mRNAs directs cellular gene silencing machinery to prevent the translation of the mRNAs. The RNAi pathway is summarized in Duan (Ed.), Section 7.3 of Chapter 7 in *Muscle Gene Therapy*, Springer Science+Business Media, LLC (2010).

As an understanding of natural RNAi pathways has developed, researchers have designed artificial miRNAs for use in regulating expression of target genes for treating disease. As described in Section 7.4 of Duan, supra, artificial miRNAs can be transcribed from DNA expression cassettes. The miRNA sequence specific for a target gene is transcribed along with sequences required to direct processing of the miRNA in a cell. Viral vectors such as adeno-associated virus have been used to deliver miRNAs to muscle [Fechner et al., *J. Mol. Med.*, 86: 987-997 (2008)].

Adeno-associated virus (AAV) is a replication-deficient parvovirus, the single-stranded DNA genome of which is about 4.7 kb in length including 145 nucleotide inverted terminal repeat (ITRs). There are multiple serotypes of AAV. The nucleotide sequences of the genomes of the AAV serotypes are known. For example, the complete genome of AAV-1 is provided in GenBank Accession No. NC_002077; the complete genome of AAV-2 is provided in GenBank Accession No. NC_001401 and Srivastava et al., *J. Virol.*, 45: 555-564 {1983); the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively; the AAV-9 genome is provided in Gao et al., *J. Virol.*, 78: 6381-6388 (2004); the AAV-10 genome is provided in *Mol. Ther.*, 13(1): 67-76 (2006); and the AAV-11 genome is provided in *Virology*, 330(2): 375-383 (2004). Cis-acting sequences directing viral DNA replication (rep), encapsidation/packaging and host cell chromosome integration are contained within the AAV ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, *Current Topics in Microbiology and Immunology*, 158: 97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is infectious as cloned DNA in plasmids which makes construction of recombinant genomes feasible. Furthermore, because the signals directing AAV replication, genome encapsidation and integration are contained within the ITRs of the AAV genome, some or all of the internal approximately 4.3 kb of the genome (encoding replication and structural capsid proteins, rep-cap) may be replaced with foreign DNA. The rep and cap proteins may be provided in trans. Another significant feature of AAV is that it is an extremely stable and hearty virus. It easily withstands the conditions used to inactivate adenovirus (56° to 65° C. for several hours), making cold preservation of AAV less critical. AAV may even be lyophilized. Finally, AAV-infected cells are not resistant to superinfection.

There remains a need in the art for a treatment for muscular dystrophies including FSHD.

SUMMARY

The present invention provides methods and products for preventing or inhibiting the expression of the DUX4 gene. The methods of the invention utilize RNAi to prevent or inhibit the expression of the DUX4 gene. The methods involve delivering inhibitory RNAs specific for the DUX4 gene to muscle cells. The DUX4 inhibitory RNAs contemplated include, but are not limited to, antisense RNAs, small inhibitory RNAs (siRNAs), short hairpin RNAs (shRNAs) or artificial microRNAs (DUX4 miRNAs) that inhibit expression of DUX4. Use of the methods and products is indicated, for example, in preventing or treating FSHD. Some embodiments of the invention exploit the unique properties of AAV to deliver DNA encoding DUX4 inhibitory RNAs to muscle cells. Other embodiments of the invention utilize other vectors (for example, other viral vectors such as adenovirus, retrovirus, lentivirus, equine-associated virus, alphavirus, pox viruses, herpes virus, polio virus, sindbis virus and vaccinia viruses) to deliver polynucleotides encoding DUX4 inhibitory RNAs.

In one aspect, the invention provides DUX4 miRNAs. In another aspect, the invention provides rAAV encoding the DUX4 miRNAs wherein the rAAV lack rep and cap genes. In some embodiments, the DUX4 miRNA comprises an miRNA antisense guide strand selected from those set out in SEQ ID NO: 10 through SEQ ID NO: 10912. These sequences comprise antisense "guide" strand sequences of the invention of varying sizes. The antisense guide strand is the strand of the mature miRNA duplex that becomes the RNA component of the RNA induced silencing complex ultimately responsible for sequence-specific gene silencing. See Section 7.3 of Duan, supra. For example, the first antisense guide strand in SEQ ID NO: 10 corresponds to (is the reverse complement of) the 3' end of the DUX4 sequence set out in FIG. 1. The second antisense guide strand (SEQ ID NO: 11) is offset one nucleotide from the first and so on. In some embodiments, the GC content of the antisense guide strand is 60% or less, and/or the 5' end of the antisense guide strand is more AU rich while the 3' end is more GC rich. Exemplified DUX4 miRNA are encoded by the DNAs are set out in SEQ ID NOs: 1 and 2.

In another aspect, the invention provides a composition comprising a rAAV encoding a DUX4 miRNA (for example, a rAAV comprising the DNA set out in SEQ ID NO: 1 or 2) wherein the rAAV lacks rep and cap genes.

In yet another aspect, the invention provides a method of preventing or inhibiting expression of the DUX4 gene in a cell comprising contacting the cell with a rAAV encoding a DUX4 miRNA (for example, a rAAV comprising the DNA set out in SEQ ID NO: 1 or 2) wherein the rAAV lacks rep and cap genes. Expression of DUX4 may be inhibited by at least 10, 20, 30, 40, 50, 60, 70, 80, 90, 95 or 99 percent.

In still another aspect, the invention provides a method of delivering DNA encoding a DUX4 miRNA to an animal in need thereof, comprising administering to the animal a rAAV a DUX4 miRNA (for example, a rAAV comprising the DNA set out in SEQ ID NO: 1 or 2) wherein the rAAV lacks rep and cap genes.

In yet another aspect, the invention provides a method of preventing or treating a muscular dystrophy (including, but not limited to, FSHD) comprising administering a rAAV encoding a DUX4 miRNA (for example, a rAAV comprising the DNA set out in SEQ ID NO: 1 or 2) wherein the rAAV lacks rep and cap genes. "Treating" includes ameliorating one or more symptoms of the muscular dystrophy (such as FSHD). Molecular, biochemical, histological and functional endpoints demonstrate the therapeutic efficacy of DUX4 miRNAs. Endpoints contemplated by the invention include one or more of: the reduction or elimination of DUX4 protein in affected muscles, DUX4 gene knockdown, increase in myofiber diameters, and improvement in muscle strength.

DETAILED DESCRIPTION

Recombinant AAV genomes of the invention comprise one or more AAV ITRs flanking a polynucleotide encoding, for example, one or more DUX4 miRNAs. The polynucleotide is operatively linked to transcriptional control DNA, specifically promoter DNA that is functional in target cells. Commercial providers such as Ambion Inc. (Austin, Tex.), Darmacon Inc. (Lafayette, Colo.), InvivoGen (San Diego, Calif.), and Molecular Research Laboratories, LLC (Herndon, Va.) generate custom inhibitory RNA molecules. In addition, commercially kits are available to produce custom siRNA molecules, such as SILENCER™ siRNA Construction Kit (Ambion Inc., Austin, Tex.) or psiRNA System (InvivoGen, San Diego, Calif.). Embodiments include a rAAV genome comprising the DNA set out in SEQ ID NO: 1 encoding the DUX4 miRNA named "miDux4.405" and a rAAV genome comprising the DNA set out in SEQ ID NO: 2 encoding the DUX4 miRNA named "miDux4.1156."

The rAAV genomes of the invention lack AAV rep and cap DNA. AAV DNA in the rAAV genomes may be from any AAV serotype for which a recombinant virus can be derived including, but not limited to, AAV serotypes AAV-1, AAV-2, AAV-3, AAV-4, AAV-5, AAV-6, AAV-7, AAV-8, AAV-9, AAV-10 and AAV-11. As noted in the Background section above, the nucleotide sequences of the genomes of various AAV serotypes are known in the art.

DNA plasmids of the invention comprise rAAV genomes of the invention. The DNA plasmids are transferred to cells permissible for infection with a helper virus of AAV (e.g., adenovirus, E1-deleted adenovirus or herpesvirus) for assembly of the rAAV genome into infectious viral particles. Techniques to produce rAAV particles, in which an AAV genome to be packaged, rep and cap genes, and helper virus functions are provided to a cell are standard in the art. Production of rAAV requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived and may be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10 and AAV-11. Production of pseudotyped rAAV is disclosed in, for example, WO 01/83692 which is incorporated by reference herein in its entirety.

A method of generating a packaging cell is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); McLaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. No. 5,786,211; U.S. Pat. No. 5,871,982; and U.S. Pat. No. 6,258,595. The foregoing documents are hereby incorporated by reference in their entirety herein, with particular emphasis on those sections of the documents relating to rAAV production.

The invention thus provides packaging cells that produce infectious rAAV. In one embodiment packaging cells may be stably transformed cancer cells such as HeLa cells, 293 cells and PerC.6 cells (a cognate 293 line). In another embodiment, packaging cells are cells that are not transformed cancer cells, such as low passage 293 cells (human fetal kidney cells transformed with E1 of adenovirus), MRC-5 cells (human fetal fibroblasts), WI-38 cells (human fetal fibroblasts), Vero cells (monkey kidney cells) and FRhL-2 cells (rhesus fetal lung cells).

Recombinant AAV (i.e., infectious encapsidated rAAV particles) of the invention comprise a rAAV genome. Embodiments include, but are not limited to, the rAAV named "AAV.miDUX4.405" including a genome encoding the DUX4 miRNA hDux.mi405 (encoded by the DNA set out in SEQ ID NO: 1 and the rAAV named "AAV.miDUX4.1156" including a genome encoding the DUX4 miRNA hDux.mi1156 (encoded by the DNA set out in SEQ ID NO: 2). The genomes of both rAAV lack AAV rep and cap DNA, that is, there is no AAV rep or cap DNA between the ITRs of the genomes.

The rAAV may be purified by methods standard in the art such as by column chromatography or cesium chloride gradients. Methods for purifying rAAV vectors from helper virus are known in the art and include methods disclosed in, for example, Clark et al., *Hum. Gene Ther.,* 10(6): 1031-1039 (1999); Schenpp and Clark, *Methods Mol. Med.,* 69 427-443 (2002); U.S. Pat. No. 6,566,118 and WO 98/09657.

In another embodiment, the invention contemplates compositions comprising rAAV of the present invention. Compositions of the invention comprise rAAV in a pharmaceutically acceptable carrier. The compositions may also comprise other ingredients such as diluents and adjuvants. Acceptable carriers, diluents and adjuvants are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics or polyethylene glycol (PEG).

Titers of rAAV to be administered in methods of the invention will vary depending, for example, on the particular rAAV, the mode of administration, the treatment goal, the individual, and the cell type(s) being targeted, and may be determined by methods standard in the art. Titers of rAAV may range from about $1\times10^6$, about $1\times10^7$, about $1\times10^8$, about $1\times10^9$, about $1\times10^{10}$, about $1\times10^{11}$, about $1\times10^{12}$, about $1\times10^{13}$ to about $1\times10^{14}$ or more DNase resistant particles (DRP) per ml. Dosages may also be expressed in units of viral genomes (vg).

Methods of transducing a target cell with rAAV, in vivo or in vitro, are contemplated by the invention. The in vivo methods comprise the step of administering an effective dose, or effective multiple doses, of a composition comprising a rAAV of the invention to an animal (including a human being) in need thereof. If the dose is administered prior to development of a disorder/disease, the administration is prophylactic. If the dose is administered after the development of a disorder/disease, the administration is therapeutic. In embodiments of the invention, an effective dose is a dose that alleviates (eliminates or reduces) at least one symptom associated with the disorder/disease state being treated, that slows or prevents progression to a disorder/disease state, that slows or prevents progression of a disorder/disease state, that diminishes the extent of disease, that results in remission (partial or total) of disease, and/or that prolongs survival. An example of a disease contemplated for prevention or treatment with methods of the invention is FSHD.

Combination therapies are also contemplated by the invention. Combination as used herein includes both simultaneous treatment or sequential treatments. Combinations of methods of the invention with standard medical treatments (e.g., corticosteroids) are specifically contemplated, as are combinations with novel therapies.

Administration of an effective dose of the compositions may be by routes standard in the art including, but not limited to, intramuscular, parenteral, intravenous, oral, buccal, nasal, pulmonary, intracranial, intraosseous, intraocular, rectal, or vaginal. Route(s) of administration and serotype(s) of AAV components of the rAAV (in particular, the AAV ITRs and capsid protein) of the invention may be chosen and/or matched by those skilled in the art taking into account the infection and/or disease state being treated and the target cells/tissue(s) that are to express the DUX4 miRNAs.

In particular, actual administration of rAAV of the present invention may be accomplished by using any physical method that will transport the rAAV recombinant vector into the target tissue of an animal. Administration according to the invention includes, but is not limited to, injection into muscle, the bloodstream and/or directly into the liver. Simply resuspending a rAAV in phosphate buffered saline has been demonstrated to be sufficient to provide a vehicle useful for muscle tissue expression, and there are no known restrictions on the carriers or other components that can be co-administered with the rAAV (although compositions that degrade DNA should be avoided in the normal manner with rAAV). Capsid proteins of a rAAV may be modified so that the rAAV is targeted to a particular target tissue of interest such as muscle. See, for example, WO 02/053703, the disclosure of which is incorporated by reference herein. Pharmaceutical compositions can be prepared as injectable formulations or as topical formulations to be delivered to the muscles by transdermal transport. Numerous formulations for both intramuscular injection and transdermal transport have been previously developed and can be used in the practice of the invention. The rAAV can be used with any pharmaceutically acceptable carrier for ease of administration and handling.

For purposes of intramuscular injection, solutions in an adjuvant such as sesame or peanut oil or in aqueous propylene glycol can be employed, as well as sterile aqueous solutions. Such aqueous solutions can be buffered, if desired, and the liquid diluent first rendered isotonic with saline or glucose. Solutions of rAAV as a free acid (DNA contains acidic phosphate groups) or a pharmacologically acceptable salt can be prepared in water suitably mixed with a surfactant such as hydroxypropylcellulose. A dispersion of rAAV can also be prepared in glycerol, liquid polyethylene glycols and mixtures thereof and in oils. Under ordinary conditions of storage and use, these preparations contain a preservative to prevent the growth of microorganisms. In this connection, the sterile aqueous media employed are all readily obtainable by standard techniques well-known to those skilled in the art.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating actions of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating rAAV in the required amount in the appropriate solvent with various other ingredients enumerated above, as required, followed by filter sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique that yield a powder of the active ingredient plus any additional desired ingredient from the previously sterile-filtered solution thereof.

Transduction with rAAV may also be carried out in vitro. In one embodiment, desired target muscle cells are removed from the subject, transduced with rAAV and reintroduced into the subject. Alternatively, syngeneic or xenogeneic muscle cells can be used where those cells will not generate an inappropriate immune response in the subject.

Suitable methods for the transduction and reintroduction of transduced cells into a subject are known in the art. In one embodiment, cells can be transduced in vitro by combining rAAV with muscle cells, e.g., in appropriate media, and screening for those cells harboring the DNA of interest using conventional techniques such as Southern blots and/or PCR, or by using selectable markers. Transduced cells can then be formulated into pharmaceutical compositions, and the composition introduced into the subject by various techniques, such as by intramuscular, intravenous, subcutaneous and intraperitoneal injection, or by injection into smooth and cardiac muscle, using e.g., a catheter.

Transduction of cells with rAAV of the invention results in sustained expression of DUX4 miRNAs. The present invention thus provides methods of administering/delivering rAAV which express DUX4 miRNAs to an animal, preferably a human being. These methods include transducing tissues (including, but not limited to, tissues such as muscle, organs such as liver and brain, and glands such as salivary glands) with one or more rAAV of the present invention. Transduction may be carried out with gene cassettes comprising tissue specific control elements. For example, one embodiment of the invention provides methods of transducing muscle cells and muscle tissues directed by muscle specific control elements, including, but not limited to, those derived from the actin and myosin gene families, such as from the myoD gene family [See Weintraub et al., Science, 251: 761-766 (1990], the myocyte-specific enhancer binding factor MEF-2 [Cserjesi and Olson, Mol Cell Biol 11: 4854-4862 (1990], control elements derived from the human skeletal actin gene [Muscat et al., Mol Cell Biol, 7: 4089-4099 (1987)], the cardiac actin gene, muscle creatine kinase sequence elements [See Johnson et al., Mol Cell Biol, 9:3393-3399 (1989)] and the murine creatine kinase enhancer (mCK) element, control elements derived from the skeletal fast-twitch troponin C gene, the slow-twitch cardiac troponin C gene and the slow-twitch troponin I gene: hypoxia-inducible nuclear factors [Semenza et al., Proc Natl Acad Sci USA, 88: 5680-5684 (1990], steroid-inducible elements and promoters including the glucocorticoid response element (GRE) [See Mader and White, Proc. Natl. Acad. Sci. USA 90: 5603-5607 (1993)], and other control elements.

Muscle tissue is an attractive target for in vivo DNA delivery, because it is not a vital organ and is easy to access. The invention contemplates sustained expression of miRNAs from transduced myofibers.

By "muscle cell" or "muscle tissue" is meant a cell or group of cells derived from muscle of any kind (for example, skeletal muscle and smooth muscle, e.g. from the digestive tract, urinary bladder, blood vessels or cardiac tissue). Such muscle cells may be differentiated or undifferentiated, such as myoblasts, myocytes, myotubes, cardiomyocytes and cardiomyoblasts.

The term "transduction" is used to refer to the administration/delivery of DUX4 miRNAs to a recipient cell either in vivo or in vitro, via a replication-deficient rAAV of the invention resulting in expression of a DUX4 miRNA by the recipient cell.

Thus, the invention provides methods of administering an effective dose (or doses, administered essentially simultaneously or doses given at intervals) of rAAV that encode DUX4 miRNAs to a patient in need thereof.

BRIEF DESCRIPTION OF THE DRAWING

FIG. 1 shows the human DUX4 DNA sequence.
In FIGS. 2A and 2B, the top sequences are the DNA templates from which each respective miRNA is transcribed.
In FIG. 2A, the DNA template miDUX4.405 is SEQ ID NO: 1.
In FIG. 2B, the DNA template miDUX4.1156 is SEQ ID NO: 2. The folded miRNA transcripts are shown as hairpin structures in FIGS. 2A and 2B.
In FIG. 2A, the miDUX4.405 folded miRNA is SEQ ID NO: 8.
In FIG. 2B, the miDUX4.1156 folded miRNA is SEQ ID NO: 9. The mature miDUX4.405 and miDUX4.1156 sequences arise following processing in target cells by host miRNA processing machinery (including Drosha, DGCR8, Dicer, and Exportin-5). Sequences shaded in gray indicate restriction sites used for cloning each miRNA into the U6T6 vector. CTCGAG is an XhoI site and ACTAGT is a SpeI site (CUCGAG and ACUAGU in RNA, where the U is a uracil base). The red sequence indicates the mature miRNA antisense guide strand that ultimately helps catalyze cleavage of the DUX4 target mRNA. This sequence is also underlined in the miRNA hairpin portions of this diagram. The gray and black arrowheads indicate Drosha- and Dicer-catalyzed cleavage sites, respectively. The numbers 13, 35, 53, and 75 are provided for orientation. The sequences between (and including) positions 35-53 are derived from the natural human mir-30a sequence, except the A at position 39, which is a G is the normal mir-30a sequence. We changed this nucleotide to an A to facilitate folding of the miRNA loop, based on in silico RNA folding models. The base of the stem (5' of position 13 and 3' of position 75) is also derived from mir-30a structure and sequence with some modifications depending on the primary sequence of the guide strand. Specifically, the nucleotide at position 13 can vary to help facilitate a required mismatched between the position 13 and 75 nucleotides. This bulged structure is hypothesized to facilitate proper Drosha cleavage.

FIG. 3 relates to a luciferase assay used for initial miDUX4 efficacy screens. FIG. 3A shows the dual luciferase reporter plasmid used for in vitro screens. This vector is modified from a commercially available plasmid (psi-Check2) obtained from Promega. The human DUX4 cDNA was cloned downstream of the Renilla luciferase gene, as shown. This conformation does not produce a Luciferase-DUX4 fusion protein, since the DUX4 sequences are placed after the Renilla luciferase stop codon. Instead, a fusion mRNA is produced, in which the DUX4 sequences are the de facto 3' untranslated region (3' UTR) of Renilla luciferase. As a result, any effective DUX4-targeted miRNA will reduce the Renilla Luciferase-DUX4 fusion mRNA, which subsequently decreases Renilla luciferase protein expression in transfected cells. There is a separate Firefly luciferase gene located on the same plasmid, which does not contain any DUX4 sequences and is therefore unaffected by DUX4-targeted miRNAs. FIG. 3B shows Firefly and Renilla luciferase activity quantified separately in cells using a Dual Luciferase Assay Kit (Promega). DUX4 gene silencing is therefore measured indirectly and indicated by a low ratio of Renilla:Firefly luciferase activity. All samples in this assay are normalized to cells co-transfected with our reporter vector and the U6.miGFP control miRNA. Samples transfected with miDUX4.405 and miDUX4.1156 had consistently lower Renilla luciferase activity, indicating DUX4 gene silencing. Data in B are representative of two independent experiments performed on different days in triplicate. Error bars indicate standard error of the mean (s.e.m.).

FIG. 4A is a diagram of constructs used in Western blot experiments showing AAV.miDUX4 proviral plasmids reduce DUX4 protein expression in vitro. In the diagram of the constructs, the black rectangles indicate AAV inverted terminal repeats (ITRs), CMV is the cytomegalovirus promoter, hrGFP is a green fluorescent protein coding region, pA is the SV40 polyA signal and V5 refers to the V5 epitope which was inserted in frame at the C terminus of human DUX4 to facilitate detection with commercially available V5 epitope antibodies (Invitrogen). The U6.miDUX4 sequences (405 and 1156) and U6.miGFP control were cloned upstream of the CMV.hrGFP.pA cassette, as shown. Proviral plasmids were co-transfected into HEK293 cells with the CMV.DUX4.V5 expression vector shown at the top of FIG. 4A. FIG. 4B shows Western blots using antibodies targeting the V5 epitope (DUX4) demonstrating DUX4 gene silencing by both miDUX4 sequences, compared to the non-targeting miGFP control. GAPDH antibodies were used to control for equivalent loading of protein extracts for the experiment. The 'Unt' lane contains protein extracts from untransfected HEK293 cells.

EXAMPLES

Figure 2A:
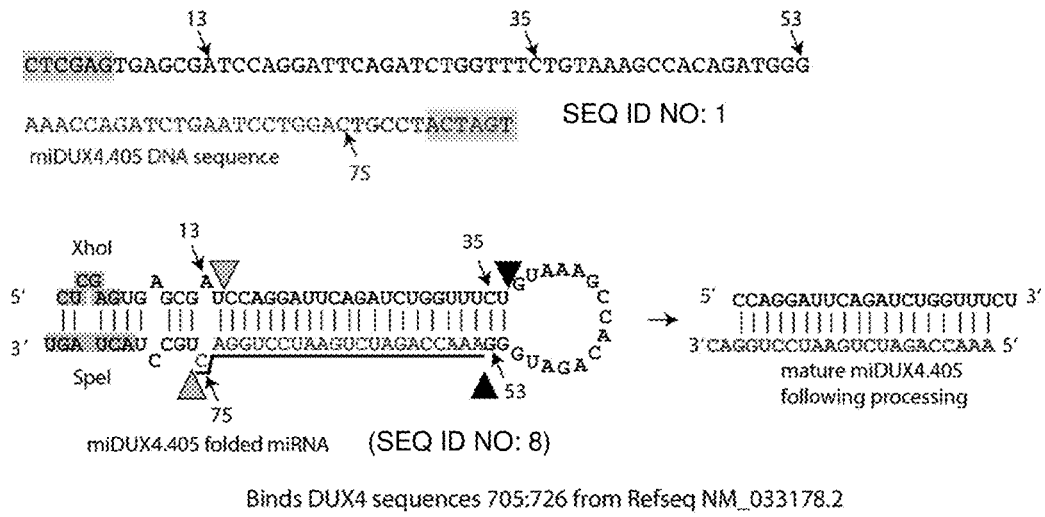
FIGS. 2A and 2B set out sequences of DUX4 targeted miRNAs.

The role of DUX4 in FSHD pathogenesis can be explained as follows. First, D4Z4 repeats are not pseudogenes. The DUX4 locus produces 1.7 kb and 2.0 kb full-length mRNAs with identical coding regions, and D4Z4 repeats also harbor smaller sense and antisense transcripts, including some resembling microRNAs. Over-expressed DUX4 transcripts and a ~50 kDa full-length DUX4 protein are found in biopsies and cell lines from FSHD patients. These data are consistent with a transcriptional de-repression model of FSHD pathogenesis. In addition, unlike pseudogenes, D4Z4 repeats and DUX4 likely have functional importance, since tandemly-arrayed D4Z4 repeats are conserved in at least eleven different placental mammalian species (non-placental animals lack D4Z4 repeats), with the greatest sequence conservation occurring within the DUX4 ORF. Second, over-expressed DUX4 is toxic to tissue culture cells and embryonic progenitors of developing lower organisms in vivo. This toxicity occurs at least partly through a pro-apoptotic mechanism, indicated by Caspase-3 activation in DUX4 transfected cells, and presence of TUNEL-positive nuclei in developmentally arrested *Xenopus* embryos injected with DUX4 mRNA at the two-cell stage. These findings are consistent with studies showing some pro-apoptotic proteins, including Caspase-3, are present in FSHD patient muscles. In addition to stimulating apoptosis, DUX4 may negatively regulate myogenesis. Human DUX4 inhibits differentiation of mouse C2C12 myoblasts in vitro, potentially by interfering with PAX3 and/or PAX7, and causes developmental arrest and reduced staining of some muscle markers when delivered to progenitor cells of zebrafish or *Xenopus* embryos. Finally, aberrant DUX4 function is directly associated with potentially important molecular changes seen in FSHD patient muscles. Specifically, full-length human DUX4 encodes an approximately 50 kDa double homeodomain transcription factor, and its only known target, Pitx1, was elevated in DUX4 over-expressing FSHD patient muscles. These data support that DUX4 catalyzes numerous downstream molecular changes that are incompatible with maintaining normal muscle integrity.

Thus, aspects and embodiments of the invention are illustrated by the following examples. Example 1 describes miRNAs specific for the DUX4 gene. Example 2 describes the effect of the miRNAs on the expression of DUX4 as measured by luciferase assay. Example 3 describes the in vitro effect of proviral plasmids expressing the miRNAs on the expression of DUX4 as measured by Western blot. Example 4 describes rAAV vectors encoding DUX4 miRNAs. Example 5 describes mitigation of DUX4-induced myopathy by AAV6.miDUX4.405 vectors. Example 6 describes protection of muscles from pathological muscles changes associated with FSHD. Example 7 describes the protection of mice from DUX4-associated grip strength deficits.

Example 1

MicroRNAs Specific for the DUX4 Gene

Two miRNAs specific for the DUX4 gene were generated by PCR. Four PCR primers were used that had the following sequences.

```
Primer 662 (miDUX4hum405F):
                                    (SEQ ID NO: 3)
AAAACTCGAGTGAGCGATCCAGGATTCAGATCTGGTTTCTGAAAGCCACA

GATGGG

Primer 663 (miDUX4hum405R):
                                    (SEQ ID NO: 4)
TTTTACTAGTAGGCAGTCCAGGATTCAGATCTGGTTTCCCATCTGTGGCT

TTCAG

Primer 665 (miDUX4hum1156F):
                                    (SEQ ID NO: 5)
AAAACTCGAGTGAGCGAAGGCGCAACCTCTCCTAGAAACTGAAAGCCACA

GATGGG

Primer 667 (miDUX4hum1156R):
                                    (SEQ ID NO: 6)
TTTTACTAGTAGGCACAGGCGCAACCTCTCCTAGAAACCCATCTGTGGCT

TTCAG
```

DNA encoding a miRNA designated hDux.mi405 was generated using primers 662 and 663. DNA encoding miRNA designated hDux.mi1156 was generated using primers 665 and 667.

Figure 2B:
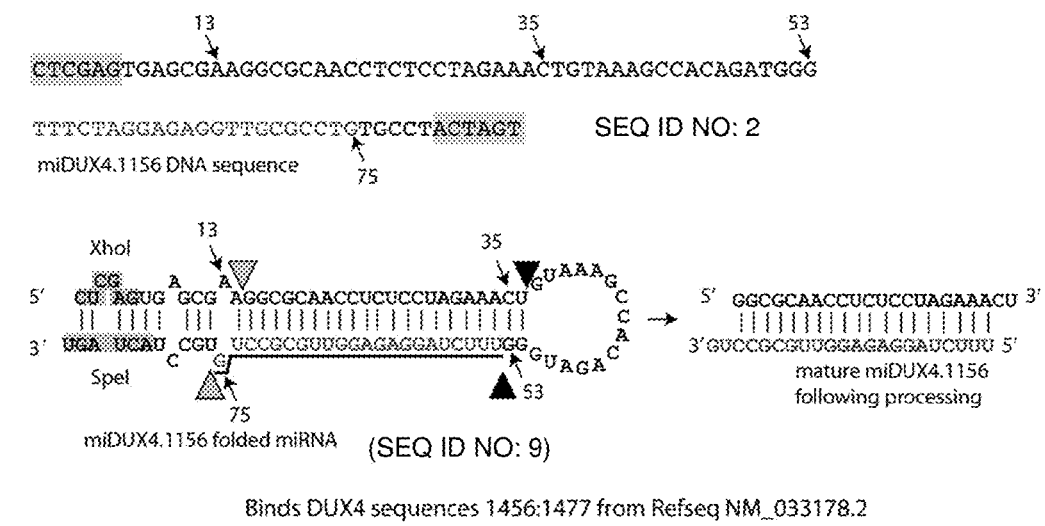

One µg of each primer was added to a 1 cycle primer extension reaction: 95° C. for 5 min.; 94° C. for 2 min.; 52° C. for 1 min.; 72° C. for 15 min.; and then holding at 4° C. The PCR products were cleaned up with the Qiagen QIAquick PCR Purification kit before being digested overnight with XHOI and SPEI restriction enzymes. The digestion product was then run on a 1.5% TBE gel and the band excised and purified using the Qiagen QIAquick Gel Extraction Kit. The sequences of the miRNAs are set out below and in FIGS. 2A and 2B, respectively.

```
miDux4.405
                                    (SEQ ID NO: 1)
CTCGAGTGAGCGATCCAGGATTCAGATCTGGTTTCTGAAAGCCACAGATG

GGAAACCAGATCTGAATCCTGGACTGCCTACTAGT miDux4.1156
                                    (SEQ ID NO: 2)
CTCGAGTGAGCGAAGGCGCAACCTCTCCTAGAAACTGAAAGCCACAGATG

GGTTTCTAGGAGAGGTTGCGCCTGTGCCTACTAGT
```

The two PCR products were ligated overnight to a U6T6 vector (via XhoI and XbaI) that contains a mouse U6 promoter and an RNA polymerase III termination signal (six thymidine nucleotides). MiRNAs are cloned into XhoI and XbaI restriction sites located between the 3' end of the U6 promoter and termination signal (SpeI site on the 3' end of the DNA template for each miRNA has complementary cohesive ends with the XbaI site). The ligation product was transformed into chemically competent *E-coli* cells with a 42° C. heat shock and incubated at 37° C. shaking for 1 hour before being plated on kanamycin selection plates. The colonies were allowed to grow overnight at 37°. The following day they were mini-prepped and sequenced for accuracy.

Example 2

Luciferase Assay for Effect of Expression of DUX4 miRNAs

Expression of the DUX4 target sequence in the presence of the DUX4 miRNAs was assayed. A lipofectamine 2000 transfection was done in 293 cells in a 96-well, white-walled assay plate. 140,000 cells were transfected with 20 ng of a Renilla-firefly plasmid containing the DUX4 target sequence (FIG. 3A) and 180 ng of various DUX4 miRNA-encoding vectors, including U6T6-driven miDux4.405 or miDux4.1156 vectors from Example 1. A luciferase assay was performed 24 hours later.

The media was removed from the cells and 20 μl of lysis buffer was added per well. The plate was put on a shaker for 15 minutes at room temperature before adding 50 μl of luciferase substrate. The first reading was taken 10 minutes later. Next, 50 μl of Stop and Glo luciferase substrate was added and the second reading was taken 10 minutes later. The Renilla expression was divided by the firefly expression to calculate the relative expression. The relative expression was then normalized to the expression of cells that were transfected with a control miRNA that targets eGFP. Results are shown in FIG. 3B. The DUX4 miRNAs miDUX4.405 and miDUX4.1156 were the most effective at reducing luciferase protein expression in transfected cells.

Example 3

Western Blot Assay for Effect of Expression of DUX4 miRNAs from rAAV

Next, the U6T6.miDUX4 miRNA expression cassettes were cloned into AAV.CMV.hrGFP proviral plasmids as shown in the FIG. 4A. The proviral plasmids were then co-transfected with a DUX4.V5 expression plasmid into 293 cells and the effect of expression of DUX4 miRNAs from the proviral plasmids was assayed by Western blot. A U6.miGFP sequence, which does not target DUX4, was used as a negative control for gene silencing.

One day before transfection, 293 cells were plated in a 24-well plate at 1.5×10$^5$ cells/well. The cells were then transfected with AAV-CMV-DUX4-V5 and AAV-CMV-miDUX4 (405 or 1156) using Lipofectamine 2000 (Invitrogen, Cat. No. 11668-019):

Group 1: AAV-CMV-DUX4-V5 50 ng+AAV-CMV-miDUX4 800 ng (1:16)
Group 2: AAV-CMV-DUX4-V5 100 ng+AAV-CMV-miDUX4 800 ng (1:8)

Thirty-six h after transfection, cells were collected and washed with cold PBS once. Seventy μl lysis buffer (137 mM NaCl, 10 mM Tris pH=7.4, 1% NP40) were then added. The cells were resuspended completely and incubated on ice for 30 min. The samples were centrifuged for 20 min at 13,000 rpm at 4° C. and the supernatant was collected. The cell lysate was diluted 5-fold for the Lowry protein concentration assay (Bio-Rad Dc Protein Assay Reagent A, B, S; Cat. No. 500-0113, 500-0114, 500-115). Twenty-three μg of each sample was taken and 2× sample buffer (100 mM Tris pH=6.8, 100 mM DTT, 10% glycerol, 2% SDS, 0.006% bromophenol blue) was added. The samples were boiled for 10 min and then put on ice.

The samples were loaded onto 10% polyacrylamide gels (based on 37.5:1 acrylamide:bis acrylamide ratio, Bio-Rad, Cat. No. 161-0158), 3.5 μg and 18 μg on two gels for each sample. Proteins were transferred to PVDF membranes at 15 V for 1 h using semi-dry transfer (Trans-Blot SD Semi-Dry Transfer Cell, Bio-Rad, Cat. No. 170-3940). The blots were placed into blocking buffer (5% non-fat dry milk, 30 mM Tris pH=7.5, 150 mM NaCl, 0.05% Tween-20) and agitated for 1 h at room temperature. The blocking buffer was decanted and anti-DUX4 primary antibody solution (DUX4 p12, Santa Cruz, Cat. No. sc-79927, 1:1,000) was added and incubated with agitation overnight at 4° C. The membranes were then washed for 30 min, changing the wash buffer (150 mM NaCl, 30 mM Tris pH=7.5, 0.05% Tween-20) every 10 min. Peroxidase-conjugated Donkey Anti-Goat Antibody (Jackson ImmunoReserch, Cat. No. 705-035-003, 1: 100, 000) was added and incubated at room temperature for 2 h. The membranes were then washed for 30 min, changing the wash buffer every 10 min. The blots were placed in chemiluminescent working solution (Immobilon Western Chemiluminescent HRP Substrate, Millipore, Cat. No. WBKLS0500), incubated with agitation for 5 min at room temperature, and then exposed to X-ray film.

The membranes were washed for 20 min, changing the wash buffer every 10 min. Next, stripping buffer (2% SDS, 62.5 mM Tris pH=6.7, 100 mM b-ME) was added to the blots and incubated at 50° C. for 30 min. The membranes were washed again for 30 min, changing the wash buffer every 10 min. Then, the membranes were blocked again and re-probed with Anti-GAPDH primary antibody solution (Chemicon, Cat. No. MAB374, 1:200) and peroxidase-conjugated Goat Anti-Mouse Antibody (Jackson ImmunoReserch, Cat. No. 115-035-146, 1:100,000) was used as secondary antibody.

Finally, the membranes were stripped again and re-probed with anti-V5 antibody (Invitrogen, Cat. No. R960-25, 1:5, 000).

The AAV.miDUX4 proviral plasmids reduced DUX4 protein expression in vitro. AAV-CMV-miDUX4.405 was the most effective at knocking down DUX4 expression.

Example 4

Production of rAAV Encoding DUX4 MicroRNAs

Vector was produced by co-transfection in HEK293 cells of three plasmids (pAdhelper, AAV helper, and the rAAV genome containing miDUX4; described in detail below), followed by cell-harvesting, vector purification, titration, and quality control assays.

Plasmids:

pAdhelper contains the adenovirus genes E2A, E4 ORF6, and VA I/II; AAV helper plasmids contain AAV rep2 and cap6 (for example, for an AAV serotype 6 preparation, the capsid gene would be called cap6); the rAAV plasmid contains AAV inverted terminal repeat (ITRs) sequences flanking the genetic elements to be packaged into the vector. For the AAV.miDUX4, this includes the U6.miDUX4 cloned upstream of the CMV.eGFP reporter gene.

Transfection:

Plasmids were transfected into 293 cells (Corning 10-Stack) using CaPO$_4$ at a 4:4:1 ratio (20 ug pAd helper:20 ug AAV helper:5 ug rAAV vector plasmid per plate.

Cell Harvesting:

Forty-eight hr post-transfection, cells were harvested and resuspended in 20 mM Tris (pH 8.0), 1 mM $MgCl_2$ and 150 mM NaCl (T20M1N150) at a density of $5\times10^6$ cells/ml. Cells were lysed by four sequential freeze/thaw cycles and Benzonase nuclease (AIC, Stock: 250 U/ul) added to a final concentration of 90 U/ml before cell lysate clarification.

Vector Purification and Titration:

Clarified lysates were subjected to iodixanol step gradient purification as previously described (Xiao, X, et al. J. Virol 72:2224-32). The 40% iodixanol layer (containing rAAV) was diluted 5-fold with a no-salt dilution buffer (pH varying depending on serotype) and applied to a Hi-Trap HP-Q/S column. Upon elution with a NaCl salt gradient, peak 1 ml fractions (typically 3-5) were pooled, dialyzed with T20M1N200 (pH 8.0), then sterile filtered and supplemented with 0.001% Pluronic F68. Vector was stored at −80° C. Purified virus was titered for vg using Q-PCR as previously described [Schnepp and Clark, *Methods Mol. Med.*, 69:427-443 (2002)].

Figure 5:
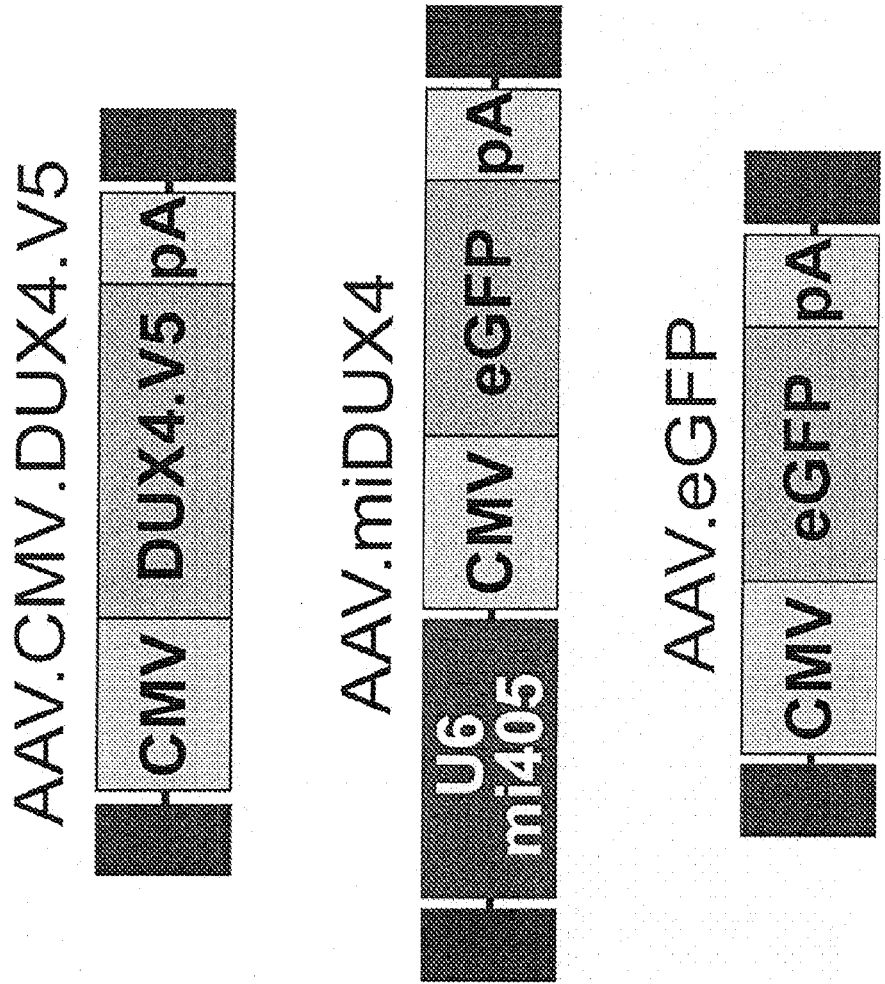
FIG. 5 is a diagram of genomes of rAAV encoding DUX4 miRNAs.

Schematic diagrams of the rAAV genomes are shown in FIG. 5.

Example 5

AAV6.miDUX4s Mitigated DUX4-Associated Muscle Toxicity In Vivo

Adult wild-type male C57BL/6 mice were co-injected with 1) $3\times10^9$ DNase resistant particles (DRP) of AAV.CMV.DUX4.V5 or were sham injected, and 2) $3\times10^{10}$ DRP of AAV.miDUX4 or control AAV.CMV.GFP into the tibialis anterior muscle. Animals were sacrificed two weeks later. Muscles were cryopreserved and cut into 10 mm cryosections, then stained with hematoxylin and eosion (H&E).

Animals that received DUX4 and eGFP vectors showed histological indicators of muscle damage. Specifically, these muscle sections contained abundant myofibers with centrally-located nuclei, small-bore myofibers (both of which indicate newly regenerated muscle), and deposition of fibrotic tissue. At 4 weeks, miDUX4-treated animals were indistinguishable from sham-injected normal wild-type muscles.

MiDUX4-treatment significantly mitigated DUX4-induced muscle degeneration, compared to control GFP-injected muscles.

Example 6

AAV6.miDUX4s Protected Muscles from Pathological Molecular Changes Associated with FSHD Caspase-3 is expressed in myofibers of FSHD patients and is activated by DUX4 expression in mouse muscle. The effect of expression of DUX4 in the presence and absence of AAV6.miDUX4 was examined.

Eight-week-old C57BL/6 female mice received 50 μl direct intramuscular injections into the tibialis anterior. Premixed virus cocktails contained $8\times10^8$ DNAse resistant particles of AAV6.DUX4 and $3\times10^{10}$ of either AAV6.miDUX4 or AAV6.eGFP. Muscle samples were prepared as described in Example 5 and stained with cleaved Caspase-3 (Cell Signaling Technology, Danvers, Mass.) polyclonal antibodies by standard methods.

Uninhibited DUX4 expression was associated with caspase-3 positive lesions in AAV6.DUX4-transduced control muscles in mice. In contrast, there were no caspase-3 positive myofibers in muscles coinjected with AAV6.DUX4 and AAV.miDUX4 vectors.

Example 7

AAV6.miDUX4s Protect Mice from DUX4-Associated Grip Strength Deficits

The effects of AAV6.miDUX4 on DUX4-associated hindlimb grip strength deficits in mice were measured.

Grip strength was measured in forelimbs and hindlimbs of C57BL/6 mice (n=8 animals) one week before injection to establish a baseline, and then weekly up to 4 weeks postinjection as previously described in Wallace et al., *Ann. Neurol.*, 69: 540-552 (2011). By two weeks, mice injected with AAV6.DUX4 alone or AAV6.DUX4 with control AAV.eGFP showed significantly reduced grip strength compared to all other groups. This timepoint is consistent with the onset of degeneration in muscle cryosections. Weakness resolved in three weeks, as regenerative processes were underway. In contrast, animals coinjected with AAV6.DUX4 and AAV6.miDUX4 were not significantly weaker than saline-injected wild type mice at any timepoint following injection. Mice that received AAV6.miDUX4 alone were unaffected, indicating miDUX4 expression was well-tolerated by normal muscles.

While the present invention has been described in terms of specific embodiments, it is understood that variations and modifications will occur to those skilled in the art. Accordingly, only such limitations as appear in the claims should be placed on the invention.

All documents referred to in this application are hereby incorporated by reference in their entirety.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09469851B2). An electronic copy of the "Sequence Listing" will also be available from the USPTO upon request and payment of the fee set forth in 37 CFR 1.19(b)(3).

We claim:

1. A recombinant adeno-associated virus comprising the nucleotide sequence of SEQ ID NO: 1 or SEQ ID NO: 2 encoding a DUX4 miRNA, wherein the recombinant adeno-associated virus lacks rep and cap genes.

2. A composition comprising the recombinant adeno-associated virus of claim 1.

3. A method of inhibiting expression of the DUX4 gene in a cell, the method comprising contacting the cell with the recombinant adeno-associated virus of claim 1 or the composition of claim 2.

4. A method of treating a facioscapulohumeral muscular dystrophy patient comprising administering to the patient by intramuscular injection a recombinant adeno-associated virus comprising nucleotide sequence of SEQ ID NO: 1 encoding a DUX4 miRNA or the nucleotide sequence of SEQ ID NO: 2 encoding a DUX4 miRNA, wherein the recombinant adeno-associated virus lacks rep and cap genes.

5. The nucleotide sequence of SEQ ID NO: 1 encoding miDUX4.405 or the nucleotide sequence of SEQ ID NO: 2 encoding miDUX4.1156.

* * * * *

UNITED STATES PATENT AND TRADEMARK OFFICE
CERTIFICATE OF CORRECTION

PATENT NO. : 9,469,851 B2
APPLICATION NO. : 14/234413
DATED : October 18, 2016
INVENTOR(S) : Scott Quenton Harper et al.

It is certified that error appears in the above-identified patent and that said Letters Patent is hereby corrected as shown below:

In the Claims

At Column 17, Line 15, "nucleotide" should be -- the nucleotide --.

Signed and Sealed this
Sixth Day of August, 2019

Andrei Iancu
*Director of the United States Patent and Trademark Office*